United States Patent [19]

Brown et al.

[11] 4,408,443
[45] Oct. 11, 1983

[54] TELECOMMUNICATIONS CABLE AND METHOD OF MAKING SAME

[75] Inventors: Robert J. Brown, Lawrenceville; Clyde J. Lever, Jr., Norcross, both of Ga.

[73] Assignee: Western Electric Company, Inc., New York, N.Y.

[21] Appl. No.: 318,524

[22] Filed: Nov. 5, 1981

[51] Int. Cl.³ ................. H01B 13/04; D07B 3/00
[52] U.S. Cl. ................................. 57/204; 57/293; 174/34
[58] Field of Search ............ 57/6, 9, 13, 204, 293, 57/294; 174/34

[56] References Cited

U.S. PATENT DOCUMENTS

| | | | |
|---|---|---|---|
| 491,109 | 2/1893 | Holman | 57/204 |
| 1,792,273 | 2/1931 | Byk et al. | 174/34 |
| 3,025,656 | 3/1962 | Cook . | |
| 3,187,495 | 6/1965 | Christian | 57/293 |
| 3,797,217 | 3/1974 | Braun . | |
| 3,823,536 | 7/1974 | Vogelsberg . | |
| 3,884,025 | 5/1975 | Oberender et al. | 57/293 |
| 3,921,381 | 11/1975 | Vogelsberg . | |
| 4,006,582 | 2/1977 | Gürkaynak et al. | 57/294 |
| 4,127,982 | 12/1978 | Braun et al. | 57/293 X |

FOREIGN PATENT DOCUMENTS 764056 12/1956 United Kingdom ............ 174/34

Primary Examiner—Donald Watkins
Attorney, Agent, or Firm—David P. Kelley

[57] ABSTRACT

A telecommunication cable, and method of making same, is disclosed comprised of more than five S-Z twisted wire pairs having their twist reversals longitudinally staggered in a repetitive sequence of 1 to N longitudinally spaced positions. The wire pairs are bundled with any adjacent pairs having their twist reversals non-overlapped and staggered by no more than N/2 positions which limits S to Z coupling.

7 Claims, 10 Drawing Figures

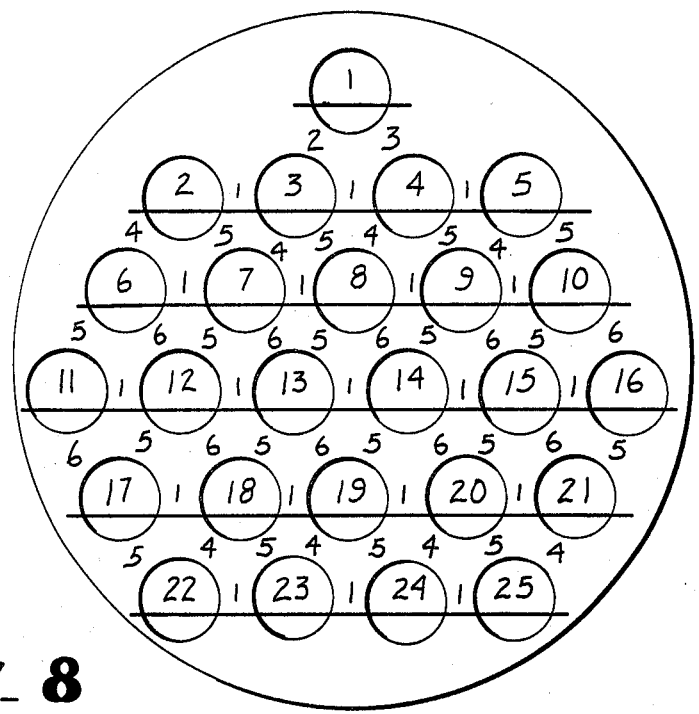
Fig_8
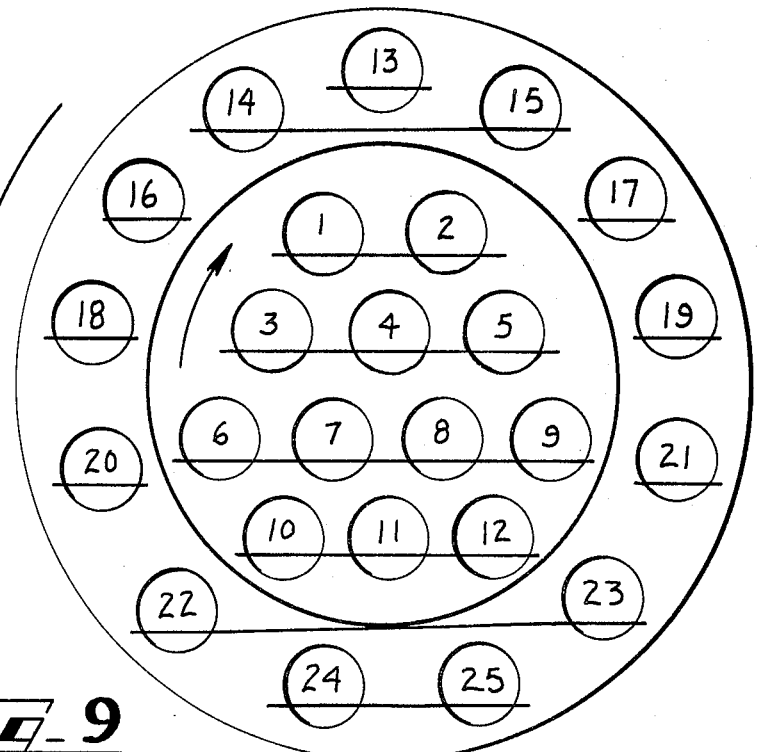
Fig_9

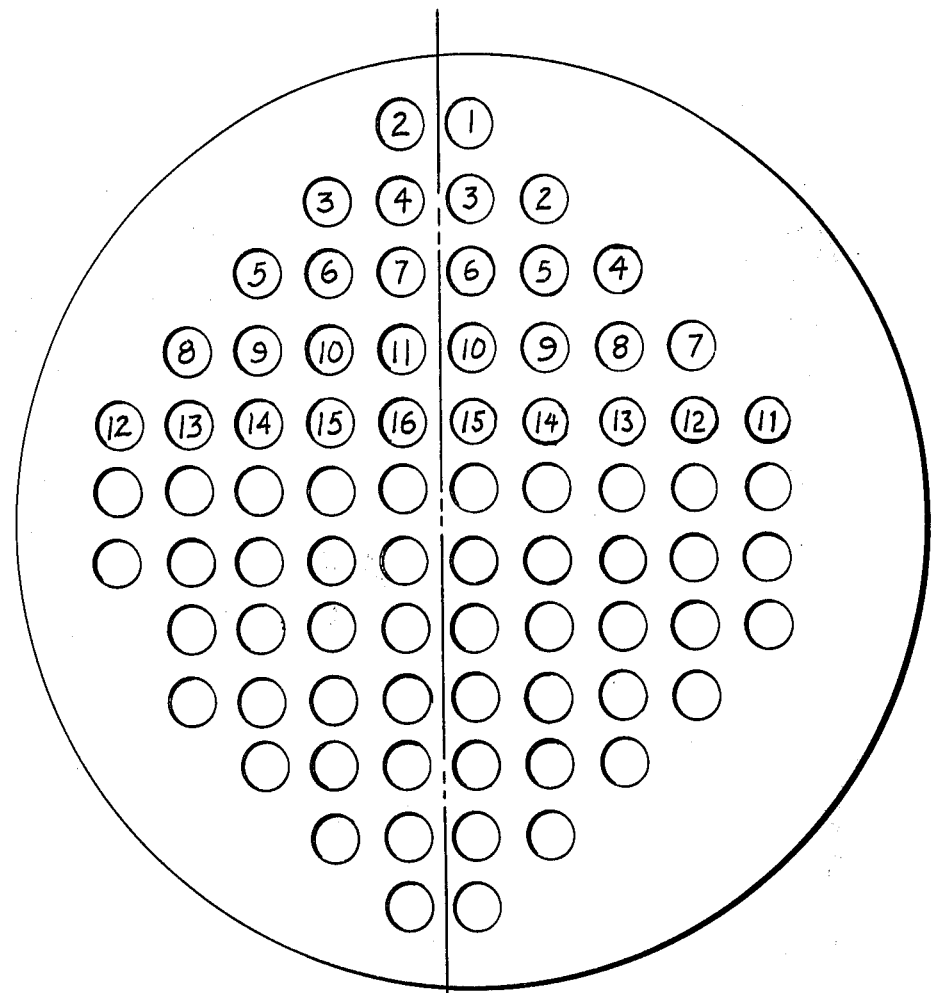
Fig_10

TELECOMMUNICATIONS CABLE AND METHOD OF MAKING SAME

TECHNICAL FIELD

This invention relates generally to telecommunication cables, and particularly to telecommunications cables of the type comprised of S-Z twisted wire pairs or quads and to methods of making them.

BACKGROUND OF THE INVENTION

Telecommunications cables are comprised of a number of twisted wire pairs or quads that are stranded together into one or more cable units. For simplicity, the term "quad" will not hereinafter be used, except in the discussion of certain prior art, with the term "pair" being intended to include quads.

In the conventional production of twisted pairs the wire supply reels, wire takeup reel, and/or an enveloping bow around the supply or takeup reel have been revolved to impart a unidirectional twist. More recently methods have been devised for forming twisted wire pairs without the need for revolving the wire supply or takeup wherein the direction of twist lay is periodically reversed. This has become known as S-Z twisting with S referring to left-hand twists and Z referring to right-hand twists. It is usually performed with the use of mutually spaced twister heads referred to as an accumulator. S-Z twisting has the distinct advantage over conventional twisting, in addition to the just-mentioned avoidance of supply or takeup rotation, of continuous operation which enables downline manufacturing operations to be tandemized with the twisting operation.

Unfortunately, telecommunications cables comprised of S-Z twisted wire pairs tend to have substantially more crosstalk than cables of conventionally twisted wire pairs. This has been determined to be attributable, in part, to the presence of wire pair sections of S twist located adjacent to wire pair sections of Z twist. Electrical coupling between S and Z pairs is much greater than between S and S pairs or Z and Z pairs. Another factor contributing to crosstalk has been the presence of parallel wire sections where the twist lay periodically reverses. Where the twist reversals of adjacent pairs are themselves adjacent to one another, that is side-by-side, coupling between the pairs is quite substantial with its magnitude depending on the length of such parallel adjacency.

The problem of crosstalk, both near end and far end, in S-Z type cable has heretofore been addressed and solutions proposed. U.S. Pat. No. 3,884,025 suggests that the quads of one layer be made to have a "different distribution function" than the pairs of adjacent layers. This different distribution function may be achieved in several ways. One way is to provide adjacent pairs with different twist lengths, a method also known for many years in conventional twisting as effective in decreasing pair coupling. While this can help, its benefits are limited since parallel and S to Z pair sections are still present. Another method is to provide different twist reversal spacings. This is essentially an averaging approach with averaging type results. A third way is to provide phase shifts, that is to rotate the conductor numbers of one quad with respect to the orientation of the conductor members of an adjacent quad. While this can be beneficial with wire quads it is of little practical use with wire pairs.

More recently it has been recognized that parallel to parallel adjacency may be lessened by staggering the reversals of wire pairs and quads having their reversals spaced apart longitudinally an equal distance. U.S. Pat. Nos. 4,006,582 and 4,127,982, for example, teach this with regard to 5-quad cables as a means of insuring that twist reversal section parallels are never adjacent. By limiting the length of reversals, no overlap can be engineered. This is an effective solution to parallel coupling in 5-quad cables, where all quads are effectively adjacent to one another, since no overlap staggering can easily be made on such a limited number of quads. Nevertheless, this provides no solution to the problem of S to Z coupling with uniform staggering since on the average half of the adjacencies are S to S or Z to Z and half are S to Z. With larger wire pair size cables only some pairs are actually adjacent and therefore potentially susceptible to the problem. But even here the S to Z coupling is still present to a large degree.

SUMMARY OF THE INVENTION

Applicants have discovered that if an arrangement is chosen so that the immediately adjacent wire pairs have their twist sections staggered by no more than half the number of stagger positions that the cable has a relatively low level of near end crosstalk. This is believed to be attributable to the restriction on S to Z coupling thereby made in combination with the elimination of parallel adjacencies.

In one form of the invention a telecommunications cable has more than five S-Z twisted wire pairs with their twist reversal sections of parallel wires longitudinally staggered in a repetitive sequence of 1 to N, where N is an integer, longitudinally spaced positions. These pairs are bundled together into a unit with any wire pairs that are adjacent to each other having their twist reversals non-overlapping and staggered by no more than N/2 positions to limit S to Z coupling.

In another form of the invention a method of manufacturing a telecommunications cable comprises the steps of forming more than five S-Z twisted wire pairs, grouping the S-Z wire pairs with their twist reversal sections longitudinally staggered in a repetitive sequence of 1 to N positions, where N is an integer, and stranding the wire pairs into a unit with the pairs organized such that any adjacent wire pairs have their twist reversals non-overlapping and staggered by no more than N/2 positions.

In yet another form of the invention a method of stranding a group of more than five S-Z twisted wire pairs having their twist reversal sections of parallel wires longitudinally staggered in a repetitive sequence of 1 to N positions, where N is an integer, into a telecommunications cable characterized by low near end crosstalk comprises the steps of advancing the more than five pairs through holes of a faceplate selected such that any adjacent wire pairs have their twist reversals non-overlapping and staggered by no more than N/2 positions.

BRIEF DESCRIPTION OF THE DRAWING

FIG. 8 is a front elevational view of a faceplate with a set of holes designated in a raster-like, multi-layered sequence;

FIG. 9 is a front elevational view of a double-disc type faceplate with each disc having a set of holes designated in a raster-like, multi-layered sequence; and FIG. 10 is a front elevational view of a faceplate with a set of holes designated in two independent raster-like, multi-layered sequences.

DETAILED DESCRIPTION

Figure 1:
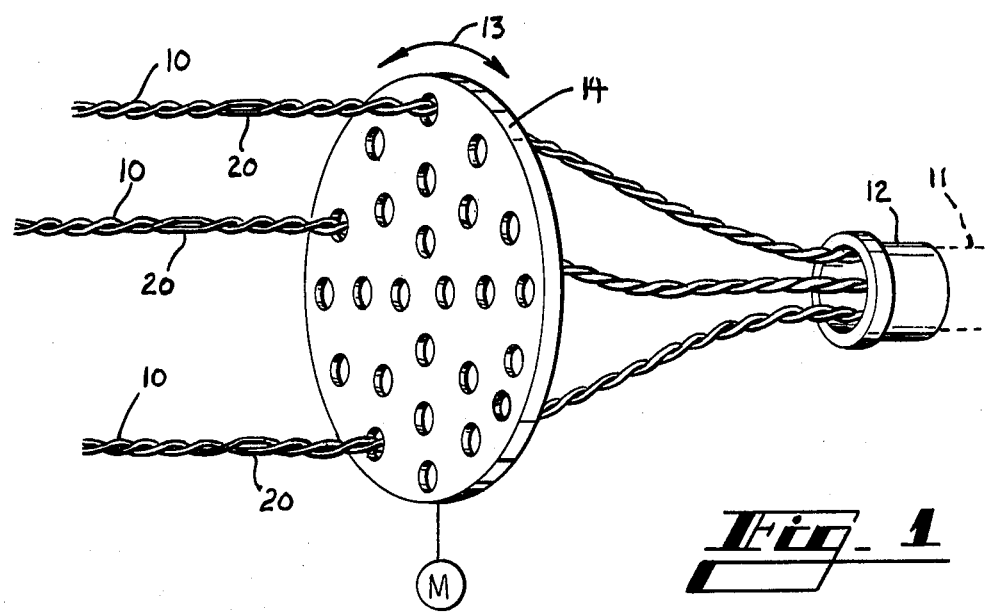
FIG. 1 is a perspective view of a single-disc type faceplate shown stranding twisted wire pairs into a unit or bundle.

Referring now in more detail to the drawing there is shown in FIG. 1 S-Z twisted wire pairs 10 being stranded into a bundle through a neck-down tube 12 by oscillatory movement indicated by arrows 13 of a faceplate 14 imparted thereto by a motor M shown schematically. For clarity only three twisted wire pairs are shown although the number of pairs would usually match the number of faceplate holes.

Figure 2:
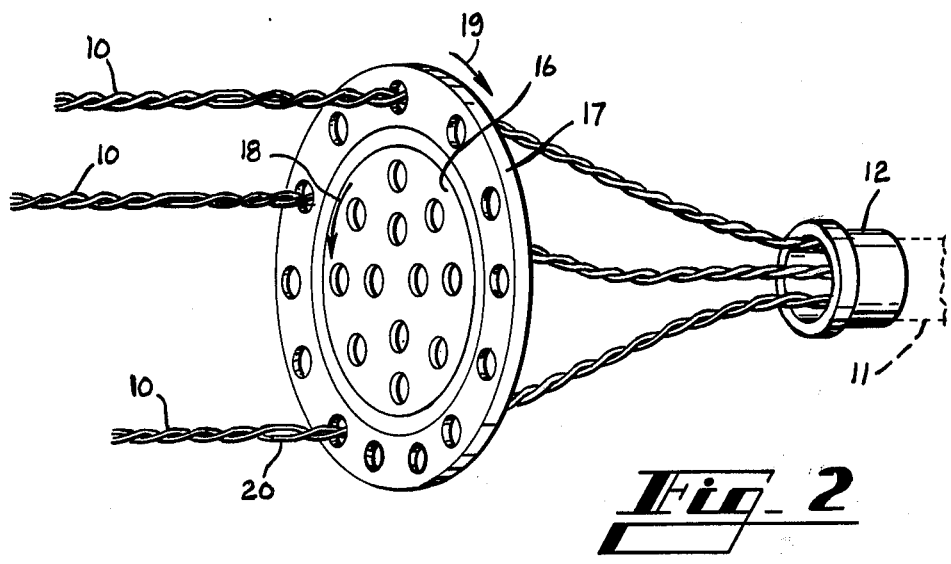
FIG. 2 is a perspective view of a double-disc type faceplate shown stranding twisted wire pairs into a unit.

Though a lay is imparted to the pairs by the oscillatory motion of the faceplate such motion is not required. In such cases a no lay cable may be formed or a lay imparted by other downline operation with the faceplate merely being used to orient or organize the pairs. Thus, the present invention is not restricted to either case. In FIG. 2 S-Z twisted wire pairs 10 are also shown being stranded into a bundle 11. Here, however, a double-disc type faceplate is employed comprised of a central disc 16 surrounded by an annular disc 17. Each disc is independently driven by unshown motor means so as to have oscillatory motion 180° out of phase with each other as indicated by arrows 18 and 19. Each of the disc has a set of holes through which twisted wire pairs are advanced. Again, for clarity, only three pairs are here shown.

Figure 3:
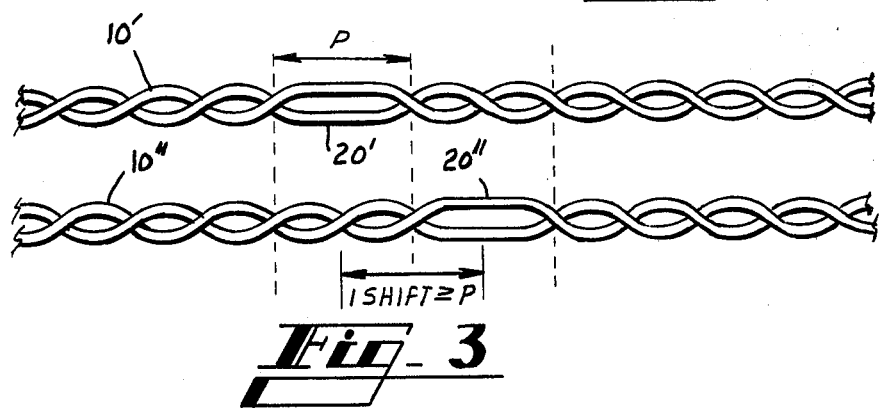
FIG. 3 is a side elevational view of two S-Z twisted wire pairs juxtaposed with their twist reversals staggered one position.

Upon close observation it will be seen that the wire pairs 10 in FIGS. 1 and 2 are S-Z twisted with their reversals 20 longitudinally staggered. As best shown in FIG. 3 each reversal section is of a length P at which section the wires of an individual pair extend side-by-side and substantially parallel. The reversals 20 for any wire pair preferably recur at fixed distances and are of generally the same length. For example, a reversal may occur each 10 to 15 feet along a wire pair with the reversal section length P being some 2 to 12 inches. However, to insure the parallel wire sections of any one pair are never side-by-side that of another pair the reversals of the several pairs are longitudinally staggered or shifted.

The stagger shown in FIG. 3 is effected with the reversal 20″ (double prime) of wire pair 10″ located to the right of reversal 20′ of wire pair 10′ by 1 shift of a length here equal to the reversal length P itself. However, as also indicated in this figure, the shift may be greater than P since such would still prevent any overlap of adjacent parallels. A constraint upon having the shift distance very much larger than P is imposed by the size requirement of twister accumulators where reversals are to be longitudinally separated by great distances to provide significant longitudinal separations, i.e., shifts between pairs in a sizable pair group.

Figure 4:
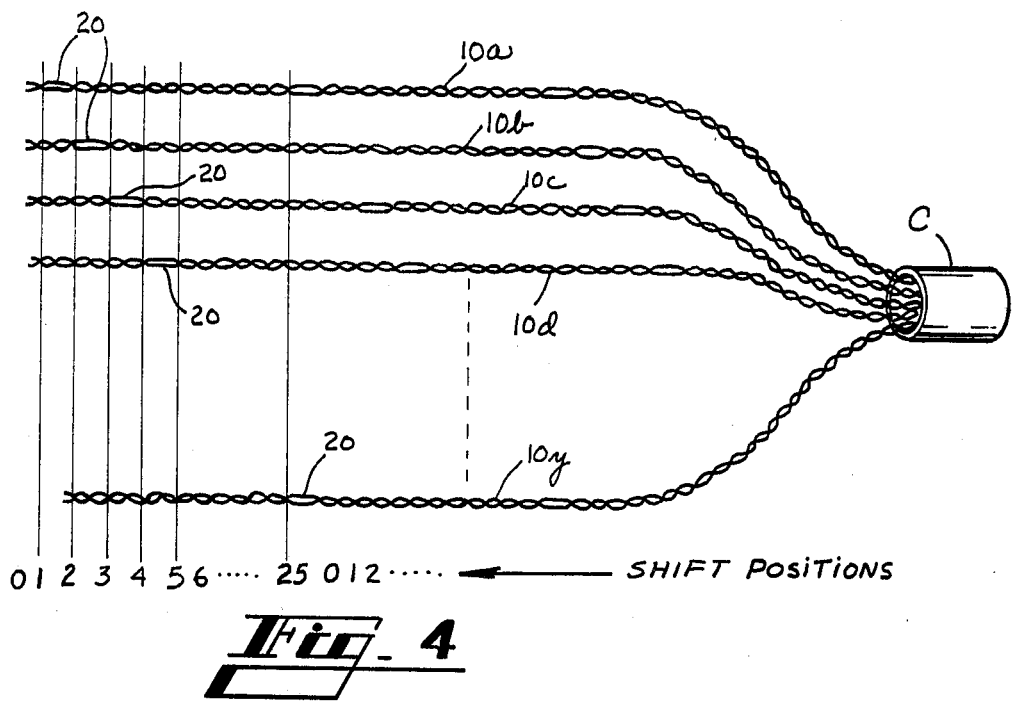
FIG. 4 is a schematic illustration of a group of twisted wire pairs that have their reversal sections longitudinally staggered which are being stranded into a cable or cable unit.

As previously stated, in accordance with the present invention wire pairs having their reversals staggered in a repetitive sequence of 1 to N positions here are passed through the holes of a faceplate selected such that wire pairs that are adjacent to one another have their twist reversal points staggered by no more than N/2 positions. FIG. 4 illustrates a sequence of positions for a 25 wire pair cable without regard to the question of adjacency wherein the pair reversals 20 are staggered in a repetitive sequence of 25 shift positions. In this case the number of positions equals the number of pairs, i.e., there are 25 positions for the 25 pairs. Here also there are no gaps between the reversals as is the case shown in FIG. 3. By definition, throughout this application shift positions are intended to be based on the assumption that in the zero (0) shift position the wire pairs are in an S to S and Z to Z orientation as opposed to S to Z.

Figure 5:
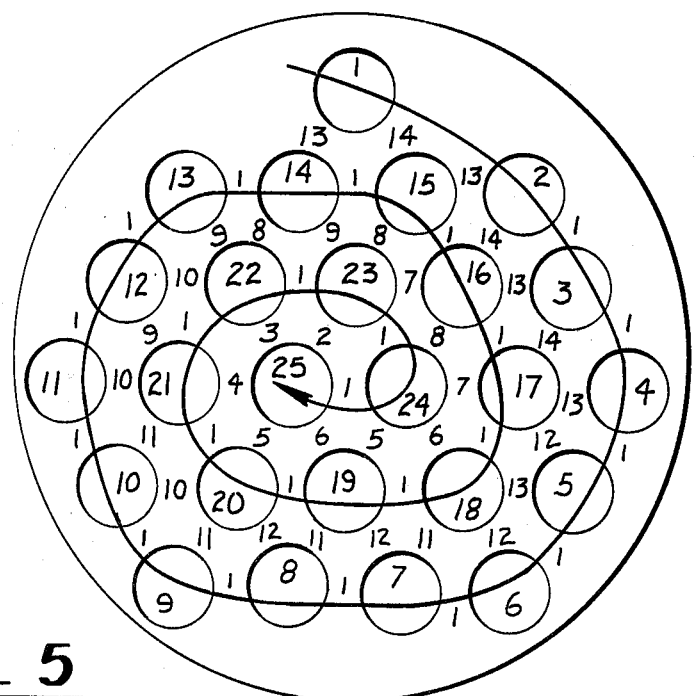
FIG. 5 is a front elevational view of a faceplate with a set of holes designated in a spiral sequence.

Turning now to FIGS. 5–10 several different hole selections for faceplates are illustrated with the number inside each hole indicating its order in a sequence with respect to reversal shift positions. The numbers between adjacent holes indicate the shift position separation of the reversals of those pairs being advanced through these holes. In FIG. 5 a spiral sequence of hole selection is shown with the pair 10a of the group shown in FIG. 4 being advanced through hole 1, pair 10b through hole 2, pair 10c through hole 3, and so forth. As the reversal stagger between pairs 10a and 10b is one shift position, the number 1 appears between holes 2 and 3, between 3 and 4, and so on. Thus, the reversals between adjacent holes in the sequence itself physically appear as in FIG. 3.

Figure 6:
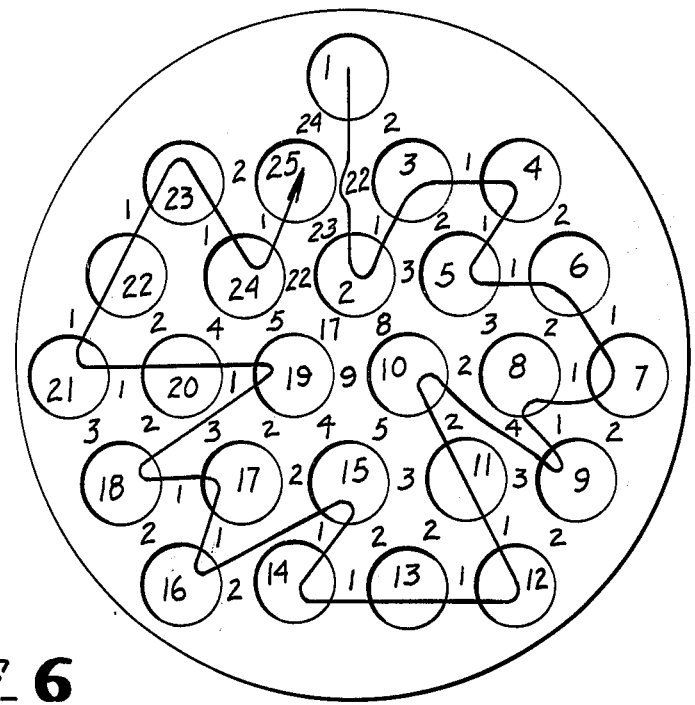
FIG. 6 is a front elevational view of a faceplate with a set of holes designated in a serpentine sequence.
Figure 7:
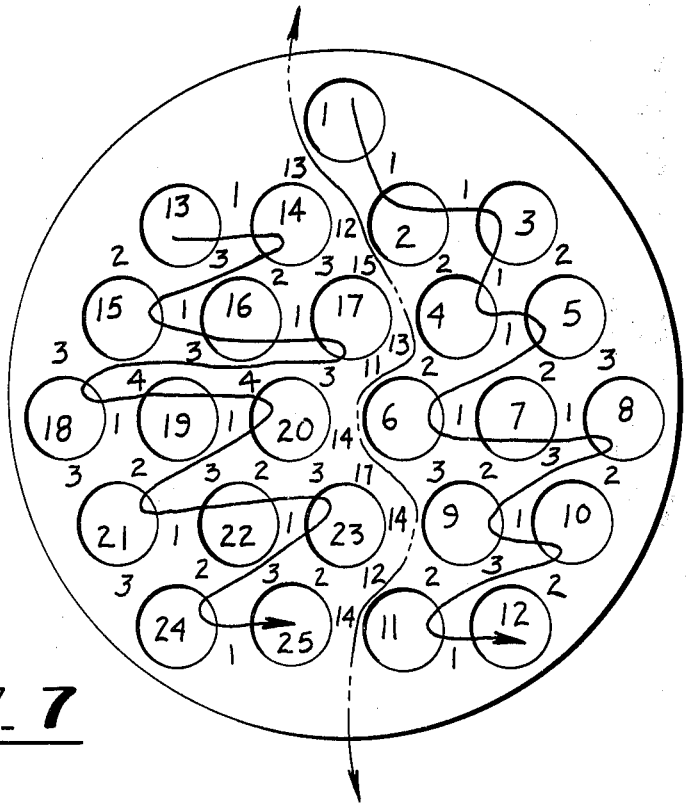
FIG. 7 is a front elevational view of a faceplate with a set of holes designated in two independent serpentine sequencies.

With reference again to FIG. 5 it is seen that the spiral sequence produces adjacencies not only of 1 shift but also of 7, 8, 9, 10, 11, 12, 13, and 14 shifts. In FIG. 6, which has a single, serpentine sequence, adjacencies of as much as 24 reversal position shifts occur. In FIG. 7, which has two independent serpentine sequences for two wire pair groups separated by the broken line, the maximum shift present is 17 positions. Now it might initially appear that no harm is done with this since there is a shift between all adjacent pairs and therefore no two parallel wire sections are presented together resulting in substantial electrical coupling. This is true with respect to that previously known point of desirability. But what this alone does not avoid is S to Z coupling.

This can be more readily appreciated by reference again to FIG. 4. Here it may be seen that all the pairs, except those with a single position shift like those of FIG. 3, inherently have both S to S and Z to Z adjacencies. With those pairs shifted by 12 and 13 positions, out of the 25 pairs of FIG. 4, they have approximately 50% S to S or Z to Z adjacency and 50% S to Z adjacency. Therefore, except for the parallel reversal points about half of their lengths are those of the undesirable S to Z situation.

With reference again to FIG. 5 it will be appreciated that those adjacent pairs staggered by but 1 position (with the numeral 1 appearing between the faceplate holes through which they are advanced as the faceplate oscillates) have no appreciable S to Z adjacency. Conversely, those shifted by some 11, 12, 13, or 14 must have almost half of their lengths in S to Z adjacent orientation. What the Applicants have discovered is that if an arrangement is chosen so that the immediately adjacent pairs have their twist reversal sections staggered by no more than half the number of stagger positions, that the cable has a relatively low level of near end crosstalk. This is believed to be attributable to the restriction on S to Z coupling in combination with the elimination of parallel adjacencies.

FIGS. 8, 9, and 10 exemplify three specific faceplate hole selection that satisfy this condition of N/2 where twist reversals are longitudinally staggered in a repetitive sequence of 1 to N longitudinally spaced positions. FIG. 8 illustrates a layered sequence for a 25 wire pair cable analagous to an electonic raster pattern. Here the pair with its reversals occupying shift position 1 is passed through the single, faceplate hole at the top. the pair with reversals at position 2 is passed through the far left hole in the second layer, the pair with reversals at position 3 through the left-of-center hole, the pair with reversals at position 4 through the right-of-center hole, and so forth. This sequence results in none of the pairs adjacent to one another being shifted by more than 6 positions. With 25 pairs N/2 is $12\frac{1}{2}$ which is substantially higher than 6. Thus, the FIG. 8 pattern does meet the N/2 requirement while the FIGS. 5, 6, and 7 patterns do not. It follows that where the wire pairs 10a–10y of FIG. 4 are advanced through the FIG. 8 faceplate, the resulting cable or cable unit C embodies principles of the invention.

FIG. 9 illustrates another pattern for use on a split-disc type faceplate that also satisfies the less than N/2 condition. Here a layered sequence is used for the annularly arranged holes of the outer disc and also for the layered or tiered holes of the central disc. In this figure pair position 1 in the inner group is shown to be adjacent to pair position 16 of the outer group with a difference of 15 which is greater than the N/2 of $12\frac{1}{2}$. However, since the two discs are rotating counter to each other their adjacency is only momentary. This transient position of adjacency is insufficient for significant coupling to occur. Therefore, for purposes of this application pairs advanced through one disc are never considered to be adjacent to or in the same layer with those advanced through another where relative motion has existed between the two discs during stranding.

FIG. 10 illustrates another pattern of hole selection for a single disc type faceplate that also satisfies the less than N/2 requirement for a 79 pair cable. This pattern is formed of two juxtaposed raster-like sequences. Here it is seen that none of the adjacencies are shifted by more than 4 positions. For example, the pair occupying hole 7 in the left side sequence is adjacent to four other pairs, namely those having shift positions of 6, 6, 4, and 11. Thus, the difference between 7 and 6 is 1, the difference between 4 and 6 is 3, and the difference between 11 and 7 is 4. A particular advantage of this pattern is that of space savings made possible by two pairs occupying the same shift position and therefore not being staggered. The non-staggered reversals, however, are not adjacent.

Actual test results have verified the benefits to be achieved when practicing the invention. The general definition of crosstalk loss between a sending wire pair i and a receiving wire pair j is as follows. Let $XT_{ij}$ be the crosstalk loss between pairs i and j. Then, by definition, $XT_{ij} = -20 \log_{10}(V_j/V_i)$ where $V_i$ and $V_j$ are voltages. The power sum crosstalk loss parameter is a standard method used to account for the crosstalk from all other pairs in a unit or cable into a receiving pair. It is defined as $$PS_j = -10 \log_{10} \left[ \sum_{\substack{i=1 \\ i \neq j}}^{\eta} \cdot 10^{-\frac{XT_{ij}}{10}} \right]$$

$\eta$ being the number of pairs in the unit or cable. More specifically, where the voltage $V_i$ is sent and measured on one end of the cable, and $V_j$ is detected and measured on the other end, then the crosstalk is termed "far end crosstalk" and the power sum parameter is termed "far end".

Tests were conducted on two 25 pair cables of 2,000 foot lengths each stranded with faceplate hole selections of the sequences illustrated in FIG. 7 and FIG. 9, respectively, but with the faceplate physically employed being that of FIG. 9 in both cases. The test was conducted with the cables having reversal sections of 6 inches average length spaced apart at recurrent intervals of 150 inches or $12\frac{1}{2}$ feet as exemplified in FIG. 3. The cable made with the FIG. 9 type sequences was found to have a 1 dB increase in average far end power sum crosstalk loss over that of the cable made with the FIG. 7 sequence. This corresponds to a 12% improvement in voltage loss into the receiving pair at 772 KHz.

When the sending voltage $V_i$ and the receiving voltage $V_j$ are both measured at the same end of the cable, then the crosstalk is termed "near end crosstalk" and the corresponding Power Sum parameter is called "near end power sum crosstalk". A 2.5 dB improvement in average near end power sum crosstalk loss, or a 33% improvement in voltage isolation into the receiving pair at the same frequency on these same cables was achieved.

It thus is seen that a new method of stranding S-Z wire pairs into a telecommunications cable of new configuration is provided that does exhibit improved crosstalk characteristics. It should be understood that the just described embodiments merely illustrates principles of the invention in selected, preferred forms. Many modifications may, however, be made thereto without departure from the spirit and scope of the invention.

What is claimed is:

1. A telecommunications cable comprised of more than five S-Z twisted wire pairs having their twist reversals longitudinally staggered in a repetitive sequence of 1 to N, where N is an integer, longitudinally spaced positions, and with said wires bundled together with any adjacent wire pairs having their twist reversals non-overlapped and staggered by no more than N/2 positions to limit S to Z coupling.

2. A telecommunications cable in accordance with claim 1 wherein the twist reversals of each wire pair are spaced apart longitudinally an equal fixed distance, whereby corresponding positions in the sequence are uniformly spaced throughout the length of the cable.

3. A telecommunications cable in accordance with claim 1 having said more than five twisted wire pairs bundled together in a plurality of layers, and wherein all adjacent wire pairs within each layer have their twist reversals staggered by one position in said sequence of staggered positions.

4. A method of manufacturing a telecommunications cable comprising the steps of:
 forming more than five S-Z twisted wire pairs;
 grouping the wire pairs with their twist reversal sections longitudinally staggered in a repetitive sequence of 1 to N positions, where N is an integer; and
 stranding the wire pairs into a unit with the pairs organized such that adjacent wire pairs have their twist reversals non-overlapping and staggered by no more than N/2 positions.

5. The method of claim 4 wherein the wire pairs are stranded into a multi-layered unit with all adjacent wire pairs within each layer having their twist reversals staggered by one position in the sequence of staggered positions.

6. A method of stranding a group of more than five S-Z twisted wire pairs having their twist reversals longitudinally staggered in a repetitive sequence of 1 to N positions, where N is an integer, into a telecommunications cable characterized by low near end crosstalk, and with the method comprising the steps of advancing the more than five pairs through holes of a faceplate selected such that adjacent wire pairs have their twist reversals non-overlapped and staggered by no more than N/2 positions.

7. The method of claim 6 wherein the faceplate holes are arranged in a plurality of layers and wherein the wire pairs having their twist reversals staggered by one position in the sequence of staggered positions are advanced through adjacent holes within common layers of holes.

* * * * *